US012594355B2

(12) United States Patent
Lant et al.

(10) Patent No.: US 12,594,355 B2
(45) Date of Patent: Apr. 7, 2026

(54) FRESHENING COMPOSITION COMPRISING BACTERIAL SPORES

(71) Applicant: The Procter & Gamble Company, Cincinnati, OH (US)

(72) Inventors: Neil Joseph Lant, Newcastle Upon Tyne (GB); Katherine Esther Latimer, Newcastle Upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 13 days.

(21) Appl. No.: 17/829,427

(22) Filed: Jun. 1, 2022

(65) Prior Publication Data

US 2023/0037662 A1 Feb. 9, 2023

(30) Foreign Application Priority Data

Jul. 19, 2021 (EP) ..................................... 21186304

(51) Int. Cl.
*A61L 2/18* (2006.01)
*D06M 16/00* (2006.01)

(52) U.S. Cl.
CPC ............ *A61L 2/18* (2013.01); *D06M 16/003* (2013.01); *A61L 2202/26* (2013.01)

(58) Field of Classification Search
CPC .... A61L 2/18; A61L 2202/26; D06M 13/005; D06M 13/148; D06M 15/03; D06M 23/06; D06M 16/00
See application file for complete search history.

(56) References Cited

U.S. PATENT DOCUMENTS

| | | | |
|---|---|---|---|
| 7,314,748 B1 | 1/2008 | Fredenburgh et al. | |
| 2021/0009922 A1 | 1/2021 | Klingman et al. | |
| 2021/0130737 A1 | 5/2021 | Njoroge et al. | |

FOREIGN PATENT DOCUMENTS

| | | | | |
|---|---|---|---|---|
| EP | 3415595 A1 | 12/2018 | | |
| EP | 3 572 492 | * 11/2019 | ............... C11D 3/50 | |
| WO | 9604939 A1 | 2/1996 | | |
| WO | WO2015130088 | * 9/2015 | ............... C11D 3/50 | |
| WO | 2017157779 A1 | 9/2017 | | |

OTHER PUBLICATIONS

PCT Search Report and Written Opinion for PCT/US2022/031674 dated Oct. 4, 2022, 12 pages.
Extended EP Search Report and Written Opinion for 21186304.8; dated Feb. 22, 2022; 7 pages.

* cited by examiner

*Primary Examiner* — Zohreh A Fay
(74) *Attorney, Agent, or Firm* — Maria Isabel Yorquez Ramirez; Andrew J. Mueller

(57) ABSTRACT

A fabric freshening composition includes from about from about $1\times10^2$ to about $1\times10^9$CFU/g of the composition, of bacterial spores; and cyclodextrins.

19 Claims, No Drawings

FRESHENING COMPOSITION COMPRISING BACTERIAL SPORES

FIELD OF THE INVENTION

The present application relates to a fabric freshening composition comprising bacterial spores and cyclodextrins. The application also relates to a product comprising a composition and a spray device and to a method of freshening a fabric using a composition.

BACKGROUND OF THE INVENTION

Products for freshening fabrics or reducing/eliminating malodors on fabrics are currently available. These products typically contain a freshening composition that includes perfume raw materials (PRMs), solvents, surfactants, and high levels of water. Having a wide variety of scent choices in freshening products enables consumers to find one that they like. Many of the existing freshening products provide instant freshening but are not capable of sustain the freshness.

There is a need for a freshening composition that provide long lasting malodor removal and/or malodor prevention.

SUMMARY OF THE INVENTION

According to a first aspect, there is provided a fabric freshening composition comprising:

a) from about $1\times10^2$ to about $1\times10^9$ CFU/g, preferably from about $1\times10^3$ to about $1\times10^7$ CFU/g of the composition, preferably from about $1\times10^4$ to about $1\times10^7$ CFU/g of the composition of bacterial spores, preferably *Bacillus* spores; and b) cyclodextrins.

The composition is preferably an aqueous liquid composition and preferably comprises surfactant and solvent and preferably a malodour counteractant and/or a setting polymer and/or an anti-wrinkle agent.

According to the second aspect, there is provided a fabric freshening product. A product comprises the freshening composition and a spray device.

According to the third aspect there is provided a method of providing sustained malodor control and prevention to a fabric using the product of the invention.

The elements of the composition of the invention described in relation to the first aspect apply mutatis mutandis to the second aspect.

DETAILED DESCRIPTION OF THE INVENTION

A composition comprises bacterial spores and cyclodextrins. It preferably comprises a perfume. The perfume comprises perfume raw materials (PRMs). PRMs are typically formulated with water to make sprayable fabric freshening compositions. However, because of the hydrophobic nature of PRMs, solvents and/or surfactants are used to solubilize and emulsify the PRMs in compositions with high water content. Solvents suitable for solubilizing PRMs typically include alcohols, polyols and mixtures thereof. Preferably, the bacterial spores are in particulate form. Preferably, the composition comprises a polysaccharide system that facilitates the suspension of the bacterial spores.

The present application includes the surprising discovery that cyclodextrins are a source of nutrients for the bacterial spores.

The term "freshening composition" as used herein refers to compositions for providing freshness on fabrics.

The term "Perfume Raw Materials" as used herein refer to perfume materials ("PRMs" or, singularly, "PRM").

The term "ClogP" as used herein refers to a calculated logP ("ClogP") value of a PRM. An octanol/water partition coefficient of a PRM is the ratio between its equilibrium concentrations in octanol and in water. The partition coefficients of the PRM used in a freshening composition may more conveniently be given in the form of its logarithm to the base 10, LogP. The ClogP is determined by a model that computes the octanol-water partition coefficient (logP or logKow) for general organic molecules based directly on molecular structure. LogP is a measure of the distribution of a solute between two immiscible liquid phases, octanol and water, and is generally used as a relative measure of the hydrophobicity of a solute. One way of computing LogP of a PRM is using the ACD/Labs LogP software module from Advanced Chemistry Development, Inc.

Details of the calculation of logP can be found on the ACD/Labs website (https://www.acdlabs.com/products/percepta/predictors/logp/). LogP values of PRMs calculating using the ACD/Labs LogP software module and the LogP values of PRMs are used in the selection of PRMs which are useful in the present invention as described hereafter in the Examples. However, it will be appreciated that another suitable way of measuring LogP is using the "ClogP" program from BioByte Corp (e.g., ClogP Version 4.0 and Manual 1999). CLOG P USER GUIDE, Version 4.0, BioByte Corp (1999) (http://www.bio-byte.com/bb/prod/clogp40.html). A further suitable way of measuring LogP is using CLOGP program from Daylight Chemical Information Systems, Inc. of Alison Viejo, CA. The CLOGP Reference manual, Daylight Version 4.9, Release Date 02/1/2008.

The term "sulfur-containing pro-perfume" as used herein refers to a type of pro-perfume compound that contains sulfur. The term "pro-perfume" as used herein refers to compounds resulting from the reaction of PRMs with other chemicals, which have a covalent bond between one or more PRMs and these chemicals. The PRM is converted into a new material called a pro-perfume compound, which then may release the original PRM (i.e. pre-converted) upon exposure to a trigger such as water or light or atmospheric oxygen. Suitable pro-perfume compounds and methods of making the same can be found in U.S. Pat. Nos. 7,018,978; 6,861,402; 6,544,945; 6,093,691; 6,165,953; and 6,096,918.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

Freshening Composition

A freshening composition comprises bacterial spores and cyclodextrins and preferably a perfume. The composition is preferably an aqueous liquid composition comprising at least 90%, preferably at least 95% and more preferably at least 98% and less than 99.5% of water by weight of the composition. Having high levels of water enable a sprayable freshening composition while minimizing any visible residues and/or stains on fabric articles. The composition can be a Newtonian fluid having a viscosity of from 1 cps to 500 cps, more preferably of from 1 cps to 300 cps, more preferably from 1 cps to 200 cps, even more preferably from 1 cps to 100 cps and most preferably from 1 cps to 50 cps and especially for 1 cps to 20 cps when measured at 20° C. with a AD1000 Advanced Rheometer from Atlas® shear rate 10 s-1 with a coned spindle of 40 mm with a cone angle 2° and a truncation of ±60 μm. The freshening composition is sprayable and the perfume remains solubilized to provide a phase-stable freshening composition that provides a consistent delivery of scent freshness in each spray.

In a preferred embodiment the bacterial spores are in particulate form and the freshening composition comprises a structurant system, preferably a polysaccharide system to suspend the particles.

Components of a freshening composition of the present invention are described in the following paragraphs.

Bacterial Spores

The spores are fabric-substantive and provide malodor control during and after the treatment of fabrics. The spores germinate when the right humidity and temperature conditions are found, and cyclodextrins seem to act as nutrients once the bacteria start to germinate.

The spores have the ability to germinate and to form cells during the treatment and continue to germinate and form cells on the fabrics using cyclodextrins as nutrients. The spores can be delivered in liquid or solid form. Preferably, the spores are in solid form.

Some gram-positive bacteria have a two-stage lifecycle in which growing bacteria under certain conditions such as in response to nutritional deprivation can undergo an elaborate developmental program leading to spores or endospores formation. The bacterial spores are protected by a coat consisting of about 60 different proteins assembled as a biochemically complex structure with intriguing morphological and mechanical properties. The protein coat is considered a static structure that provides rigidity and mainly acting as a sieve to exclude exogenous large toxic molecules, such as lytic enzymes. Spores play critical roles in long term survival of the species because they are highly resistant to extreme environmental conditions. Spores are also capable of remaining metabolically dormant for years. Methods for obtaining bacterial spores from vegetative cells are well known in the field. In some examples, vegetative bacterial cells are grown in liquid medium. Beginning in the late logarithmic growth phase or early stationary growth phase, the bacteria may begin to sporulate. When the bacteria have finished sporulating, the spores may be obtained from the medium, by using centrifugation for example. Various methods may be used to kill or remove any remaining vegetative cells. Various methods may be used to purify the spores from cellular debris and/or other materials or substances. Bacterial spores may be differentiated from vegetative cells using a variety of techniques, like phase-contrast microscopy, automated scanning microscopy, high resolution atomic force microscopy or tolerance to heat, for example. Because bacterial spores are generally environmentally-tolerant structures that are metabolically inert or dormant, they are readily chosen to be used in commercial microbial products. Despite their ruggedness and extreme longevity, spores can rapidly respond to the presence of small specific molecules known as germinants that signal favorable conditions for breaking dormancy through germination, an initial step in the process of completing the lifecycle by returning to vegetative bacteria. For example, the commercial microbial products may be designed to be dispersed into an environment where the spores encounter the germinants present in the environment to germinate into vegetative cells and perform an intended function. A variety of different bacteria may form spores. Bacteria from any of these groups may be used in the compositions, methods, and kits disclosed herein. For example, some bacteria of the following genera may form spores: *Acetonema, Alkalibacillus, Ammoniphilus, Amphibacillus, Anaerobacter*, Anaerospora, *Aneurinibacillus, Anoxybacillus, Bacillus, Brevibacillus, Caldanaerobacter, Caloramator, Caminicella, Cerasibacillus, Clostridium, Clostridiisalibacter, Cohnella, Dendrosporobacter, Desulfotomaculum, Desulfosporomusa, Desulfosporosinus, Desulfovirgula, Desulfunispora, Desulfurispora, Filifactor, Filobacillus, Gelria, Geobacillus, Geosporobacter, Gracilibacillus, Halonatronum, Heliobacterium, Heliophilum, Laceyella, Lentibacillus, Lysinibacillus, Mahella, Metabacterium, Moorella, Natroniella, Oceanobacillus, Orenia, Ornithinibacillus, Oxalophagus, Oxobacter, Paenibacillus, Paraliobacillus, Pelospora, Pelotomaculum, Piscibacillus, Planifilum, Pontibacillus, Propionispora, Salinibacillus, Salsuginibacillus, Seinonella, Shimazuella, Sporacetigenium, Sporoanaerobacter, Sporobacter, Sporobacterium, Sporohalobacter, Sporolactobacillus, Sporomusa, Sporosarcina, Sporotalea, Sporotomaculum, Syntrophomonas, Syntrophospora, Tenuibacillus, Tepidibacter, Terribacillus, Thalassobacillus, Thermoacetogenium, Thermoactinomyces, Thermoalkalibacillus, Thermoanaerobacter, Thermoanaeromonas, Thermobacillus, Thermoflavimicrobium, Thermovenabulum, Tuberibacillus, Virgibacillus*, and/or *Vulcanobacillus*.

Preferably, the bacteria that may form spores are from the family Bacillaceae, such as species of the genera *Aeribacillus, Aliibacillus, Alkalibacillus, Alkalicoccus, Alkalihalobacillus, Alkalilactibacillus, Allobacillus, Alteribacillus, Alteribacter, Amphibacillus, Anaerobacillus, Anoxybacillus, Aquibacillus, Aquisalibacillus, Aureibacillus, Bacillus, Caldalkalibacillus, Caldibacillus, Calditerricola, Calidifontibacillus, Camelliibacillus, Cerasibacillus, Compostibacillus, Cytobacillus, Desertibacillus, Domibacillus, Ectobacillus, Evansella, Falsibacillus, Ferdinandcohnia, Fermentibacillus, Fictibacillus, Filobacillus, Geobacillus, Geomicrobium, Gottfriedia, Gracilibacillus, Halalkalibacillus, Halobacillus, Halolactibacillus, Heyndrickxia, Hydrogenibacillus, Lederbergia, Lentibacillus, Litchfieldia, Lottiidibacillus, Margalitia, Marinococcus, Melghiribacillus, Mesobacillus, Metabacillus, Microaerobacter, Natribacillus, Natronobacillus, Neobacillus, Niallia, Oceanobacillus, Ornithinibacillus, Parageobacillus, Paraliobacillus, Paralkalibacillus, Paucisalibacillus, Pelagirhabdus, Peribacillus, Piscibacillus, Polygonibacillus, Pontibacillus, Pradoshia, Priestia, Pseudogracilibacillus, Pueribacillus, Radiobacillus, Robertmurraya, Rossellomorea, Saccharococcus, Salibacterium, Salimicrobium, Salinibacillus, Salipaludibacillus, Salirhabdus, Salisediminibacterium, Saliterribacillus, Salsuginibacillus, Sediminibacillus, Siminovitchia, Sinibacillus, Sinobaca, Streptohalobacillus, Sutcliffiella, Swionibacillus, Tenuibacillus, Tepidibacillus, Terribacillus, Terrilactibacillus, Texcoconibacillus, Thalassobacillus, Thalassorhabdus, Thermolongibacillus, Virgibacillus, Viridibacillu, Vulcanibacillus, Weizmannia*. In various examples, the bacteria may be strains of *Bacillus Bacillus* acidicola, *Bacillus aeolius, Bacillus aerius, Bacillus aerophilus, Bacillus albus, Bacillus altitudinis, Bacillus alveayuensis, Bacillus amyloliquefaciensex, Bacillus anthracis, Bacillus* aquiflavi, *Bacillus atrophaeus, Bacillus australimaris, Bacillus badius, Bacillus benzoevorans, Bacillus cabrialesii, Bacillus canaveralius, Bacillus capparidis, Bacillus carboniphilus, Bacillus cereus, Bacillus chungangensis, Bacillus coahuilensis, Bacillus cytotoxicus, Bacillus* decisifrondis, *Bacillus* ectoiniformans, *Bacillus* enclensis, *Bacillus* fengqiuensis, *Bacillus fungorum, Bacillus* glycinifermentans, *Bacillus* gobiensis, *Bacillus halotolerans, Bacillus haynesii, Bacillus horti, Bacillus inaquosorum, Bacillus infantis, Bacillus infernus, Bacillus isabeliae, Bacillus kexueae, Bacillus licheniformis, Bacillus luti, Bacillus manusensis, Bacillus marinisedimentorum, Bacillus mesophilus, Bacillus methanolicus, Bacillus mobilis, Bacillus mojavensis, Bacillus mycoides, Bacillus nakamurai, Bacillus ndiopicus, Bacillus nitratireducens, Bacillus oleivorans, Bacillus pacificus, Bacillus pakistanensis, Bacillus paralicheniformis, Bacillus paramycoides, Bacillus paranthracis, Bacillus pervagus, Bacillus piscicola, Bacillus proteolyticus, Bacillus pseudomycoides, Bacillus pumilus, Bacillus safensis, Bacillus salacetis, Bacillus salinus, Bacillus salitolerans, Bacillus seohaeanensis, Bacillus shivajii, Bacillus siamensis, Bacillus smithii, Bacillus solimangrovi, Bacillus songklensis, Bacillus sonorensis, Bacillus spizizenii, Bacillus spongiae, Bacillus stercoris, Bacillus stratosphericus, Bacillus subtilis, Bacillus swezeyi, Bacillus taeanensis, Bacillus tamaricis, Bacillus tequilensis, Bacillus thermocloacae, Bacillus thermotolerans, Bacillus thuringiensis, Bacillus tianshenii, Bacillus toyonensis, Bacillus tropicus, Bacillus vallismortis, Bacillus velezensis, Bacillus wiedmannii, Bacillus wudalianchiensis, Bacillus xiamenensis, Bacillus xiapuensis, Bacillus* zhangzhouensis, or combinations thereof.

In some examples, the bacterial strains that form spores may be strains of *Bacillus*, including: *Bacillus* sp. strain SD-6991; *Bacillus* sp. strain SD-6992; *Bacillus* sp. strain NRRL B-50606; *Bacillus* sp. strain NRRL B-50887; *Bacillus pumilus* strain NRRL B-50016; *Bacillus amyloliquefaciens* strain NRRL B-50017; *Bacillus amyloliquefaciens* strain PTA-7792 (previously classified as *Bacillus atrophaeus*); *Bacillus amyloliquefaciens* strain PTA-7543 (previously classified as *Bacillus atrophaeus*); *Bacillus amyloliquefaciens* strain NRRL B-50018; *Bacillus amyloliquefaciens* strain PTA-7541; *Bacillus amyloliquefaciens* strain PTA-7544; *Bacillus amyloliquefaciens* strain PTA-7545; *Bacillus amyloliquefaciens* strain PTA-7546; *Bacillus subtilis* strain PTA-7547; *Bacillus amyloliquefaciens* strain PTA-7549; *Bacillus amyloliquefaciens* strain PTA-7793; *Bacillus amyloliquefaciens* strain PTA-7790; *Bacillus amyloliquefaciens* strain PTA-7791; *Bacillus subtilis* strain NRRL B-50136 (also known as DA-33R, ATCC accession No. 55406); *Bacillus amyloliquefaciens* strain NRRL B-50141; *Bacillus amyloliquefaciens* strain NRRL B-50399; *Bacillus licheniformis* strain NRRL B-50014; *Bacillus licheniformis* strain NRRL B-50015; *Bacillus amyloliquefaciens* strain NRRL B-50607; *Bacillus* subtilisstrain NRRL B-50147 (also known as 300R); *Bacillus amyloliquefaciens* strain NRRL B-50150; *Bacillus amyloliquefaciens* strain NRRL B-50154; *Bacillus megaterium* PTA-3142; *Bacillus amyloliquefaciens* strain ATCC accession No. 55405 (also known as 300); *Bacillus amyloliquefaciens* strain ATCC accession No. 55407 (also known as PMX); *Bacillus pumilus* NRRL B-50398 (also known as ATCC 700385, PMX-1, and NRRL B-50255); *Bacillus cereus* ATCC accession No. 700386; *Bacillus thuringiensis* ATCC accession No. 700387 (all of the above strains are available from Novozymes, Inc., USA); *Bacillus amyloliquefaciens* FZB24 (e.g., isolates NRRL B-50304 and NRRL B-50349 TAEGRO® from Novozymes), *Bacillus subtilis* (e.g., isolate NRRL B-21661 in RHAPSODY®, SERENADE® MAX and SERENADE® ASO from Bayer CropScience), *Bacillus pumilus* (e.g., isolate NRRL B-50349 from Bayer CropScience), *Bacillus amyloliquefaciens* TrigoCor (also known as "TrigoCor 1448"; e.g., isolate Embrapa Trigo Accession No. 144/88.4Lev, Cornell Accession No.Pma007BR-97, and ATCC accession No. 202152, from Cornell University, USA) and combinations thereof.

In some examples, the bacterial strains that form spores may be strains of *Bacillus amyloliquefaciens*. For example, the strains may be *Bacillus amyloliquefaciens* strain PTA-7543 (previously classified as *Bacillus atrophaeus*), and/or *Bacillus amyloliquefaciens* strain NRRL B-50154, *Bacillus amyloliquefaciens* strain PTA-7543 (previously classified as *Bacillus atrophaeus*), *Bacillus amyloliquefaciens* strain NRRL B-50154, or from other *Bacillus amyloliquefaciens* organisms.

In some examples, the bacterial strains that form spores may be *Brevibacillus* spp., e.g., *Brevibacillus brevis; Brevibacillus formosus; Brevibacillus laterosporus*; or *Brevibacillus parabrevis*, or combinations thereof.

In some examples, the bacterial strains that form spores may be *Paenibacillus* spp., e.g., *Paenibacillus alvei; Paenibacillus amylolyticus; Paenibacillus azotofixans; Paenibacillus cookii; Paenibacillus macerans; Paenibacillus polymyxa; Paenibacillus validus*, or combinations thereof. The bacterial spores may have an average particle diameter of about 2-50 microns, suitably about 10-45 microns. *Bacillus* spores are commercially available in blends in aqueous carriers and are insoluble in the aqueous carriers. Other commercially available *bacillus* spore blends include without limitation Freshen Free™ CAN (10X), available from Novozymes Biologicals, Inc.; Evogen® Renew Plus (10X), available from Genesis Biosciences, Inc.; and Evogen® GT (10X, 20X and 110X), all available from Genesis Biosciences, Inc. In the foregoing list, the parenthetical notations (10X, 20X, and 110X) indicate relative concentrations of the *Bacillus* spores.

Bacterial spores used in the compositions, methods, and products disclosed herein may or may not be heat activated. In some examples, the bacterial spores are heat activated. In some examples, the bacterial spores are not heat inactivated. Preferably, the spores used herein are heat activated. Heat activation may comprise heating bacterial spores from room temperature (15-25° C.) to optimal temperature of between 25-120° C., preferably between 40 C-100° C., and held the optimal temperature for not more than 2 hours, preferably between 70-80° C. for 30 min.

For the composition disclosed herein, populations of bacterial spores are generally used. In some examples, a population of bacterial spores may include bacterial spores from a single strain of bacterium. Preferably, a population of bacterial spores may include bacterial spores from 2, 3, 4, 5, or more strains of bacteria. Generally, a population of bacterial spores contains a majority of spores and a minority of vegetative cells. In some examples, a population of bacterial spores does not contain vegetative cells. In some examples, a population of bacterial spores may contain less than about 1%, 2%, 3%, 4%, 5%, 6%, 7%, 8%, 9%, 10%, 15%, 20%, 25%, 30%, 40%, or 50% vegetative cells, where the percentage of bacterial spores is calculated as ((vegetative cells/(spores in population+vegetative cells in population))×100). Generally, populations of bacterial spores used in the disclosed methods, compositions and products are stable (i.e. not undergoing germination), with at least some individual spores in the population capable of germinating.

Populations of bacterial spores used in this disclosure may contain bacterial spores at different concentrations. In various examples, populations of bacterial spores may contain, without limitation, at least $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1 \times 10^8$, $5 \times 10^8$, $1 \times 10^9$, $5 \times 10^9$, $1 \times 10^{10}$ , $5 \times 10^{10}$ , $1 \times 10^{11}$ $5 \times 10^{11}$ $5 \times 10^{11}$, $1 \times 10^{12}$, $5 \times 10^{12}$, $1 \times 10^{13}$, $5 \times 10^{13}$, $1 \times 10^{14}$, or $5 \times 10^{14}$ spores/ml, spores/gram, or spores/$cm^3$.

Preferably, the bacterial spores comprise *Bacillus* spores, more preferably *Bacillus* selected from the group consisting of *Bacillus subtilis, Bacillus amyloliquefaciens, Bacillus licheniformis, Bacillus megaterium, Bacillus pumilus, Bacillus cereus, Bacillus thuringiensis, Bacillus mycoides, Bacillus tequilensis, Bacillus vallismortis, Bacillus mojavensis* and mixtures thereof, more preferably selected from the group consisting of *Bacillus subtilis, Bacillus amyloliquefaciens, Bacillus licheniformis, Bacillus megaterium, Bacillus pumilus* and mixtures thereof.

Perfume Composition (Hereinafter "Perfume")

The freshening composition comprises a perfume formulated in an effective amount such that it provides a desired scent characteristic and can be homogenously solubilized in the freshening composition to deliver a consistent release profile. The perfume preferably comprises at least 60% by weight of the perfume of Perfume Raw Materials (PRMs) having a ClogP value greater than 1.0. The perfume may be in an amount of at least 0.001%, from 0.002% to 3%, from 0.005% to 1%, from 0.005% to 0.4% by weight of the composition. Suitable perfumes, perfume ingredients, and perfume carriers are disclosed in U.S. Pat. No. 5,500,138 and U.S. Publication No. 2002/0035053A1.

Any type of perfume can be incorporated into the composition of the present invention. The preferred perfume ingredients are those suitable for use for application on fabrics and garments. Typical examples of such preferred ingredients are given in U.S. Pat. No. 5,445,747.

The PRMs may be defined by their boiling point ("B.P.") and octanol/water partition coefficient ("P"). The boiling point referred to herein is measured under normal standard pressure of 760 mmHg. The boiling points of many PRMs, at standard 760 mm Hg, are outlined in "Perfume and Flavor Chemicals (Aroma Chemicals)," written and published by Steffen Arctander, 1969.

When long lasting fragrance odor on fabrics is desired, it is preferred to use at least an effective amount of perfume ingredients which have a boiling point of about 240° C. or higher and preferably of about 250° C. or higher. Nonlimiting examples of such preferred ingredients are given in U.S. Pat. No. 5,500,138.

Other perfume ingredients can act as solvents. In some cases this can help facilitate the incorporation of other perfume or oil ingredients into the overall composition. A particularly good example here is benzyl alcohol. Benzyl alcohol has limited water solubility (clogP of about 1.2) and has been shown to help incorporate other perfume ingredient mixes into these compositions.

Sulfur-Containing Pro-Perfume

The freshening composition may comprise a sulfur-containing pro-perfume. A technical effect of the sulfur-containing pro-perfume is that it improves the stability of freshening compositions. The sulfur-containing pro-perfume compound may be present at various levels in the composition. Specifically, the freshening composition may comprise from about 0.001% to about 5%, alternatively from about 0.001% to about 3%, alternatively from about 0.01% to about 1%, alternatively about 0.01% to about 0.5%, alternatively about 0.01% to about 0.1%, alternatively at least about 0.02%, or different combinations of the upper and lower percentages described above or combinations of any integer in the ranges listed above of a sulfur-containing pro-perfume by weight of the freshening composition.

The freshening composition may comprise dodecyl thio-damascone having the general structure shown below.

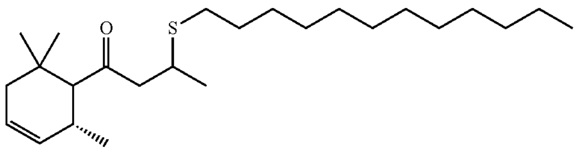 [SMILES: CCCCCCCCCCCCSC(C)CC(=O)C1[C@H](C)C=CCC1(C)C]

Thio-damascone may be present in an amount form about 0.001% to about 1.0%, alternatively from about 0.001% to about 5.0%, alternative from about 0.001% to about 3.0%, alternatively from about 0.01% to about 1.0%, alternatively about 0.01% to about 0.5%, alternative about 0.01% to about 0.1%, alternatively at least about 0.02% by weight of the freshening composition.

The weight ratio of perfume mixture to sulfur-containing pro-perfume may be about 0.01:1 to about 200:1, or about 5:1 to about 50:1, or about 10:1 to about 40:1, or about 10:1 to about 20:1, by weight of the composition.

Solvents

The freshening composition may comprise a solvent for solubilizing the perfume. Specifically, the composition may comprise less than 10%, from 0.01% to 5%, from 0.01% to 3%, from 0.01% to 1%, from 0.01% to 0.05% by weight of the freshening composition. The solvent may be selected from a group consisting of: an alcohol, a polyol and mixtures thereof. The solvent may comprise low molecular weight monohydric alcohols (e.g., ethanol, methanol, and isopropanol, or polyols, such as ethylene glycol and propylene glycol).

Alkoxylated Phenol

The freshening composition might comprise an alkoxylated phenol in a level of at least 0.0015% by weight of the composition. Without wishing to be bound by theory, use of alkoxylated phenols relative to use of traditional solvents such as ethanol to solubilize perfumes in freshening compositions is alkoxylated phenols have the combination of a phenol functional group and an ether functional group in the same molecule which provides unique solvency characteristics with both polar and non-polar properties. This surfactant-like structure gives alkoxylated phenols the ability to couple unlike liquid phases of ingredients used for freshening compositions (e.g. water and perfume as described hereinafter) and be miscible in a broad range of hydrophilic and hydrophobic solvents.

Surfactants

The freshening composition may contain a surfactant to solubilize any excess hydrophobic organic materials, particularly any PRMs, and also optional ingredients (e.g., insect repelling agent, antioxidant, etc.) which can be added to the composition, that are not readily soluble in the composition, to form a clear solution. The freshening composition may comprise less than 3.5%, from 0.01% to 3%, from 0.01% to 1%, from 0.01% to 0.05% by weight of the freshening composition. A suitable surfactant is a no-foaming or low-foaming surfactant. The surfactant may be selected from the group consisting of: nonionic surfactants, cationic surfactants, amphoteric surfactants, zwitterionic surfactants and mixtures thereof.

Malodor Binding Polymer

The freshening composition of the present invention may comprise a malodor binding polymer. A malodor binding polymer is polymer having an available functional group (e.g. amine) that has the affinity to neutralize malodor components. Monomers having an available function group with an affinity to neutralize malodor components are also contemplated. In the case of amine based compounds, the amine will have an affinity for aldehyde malodors. The amine may react with aldehyde malodors and form a new compound, such as an aminol, imine, or enamine which is not odorous.

A malodor binding polymer may include amine based compounds, such as monoamines, amino acids, polyethyleneimine polymers (PEIs), modified PEIs, substituted PEIs; acrylic acid polymers, such as polyacrylate co-polymer (e.g. Acumer™ 9000 from Rohm & Haas), polyacrylic acid polymers (e.g. Acusol™ from Rohm & Haas), and modified acrylate copolymers (e.g. Aculyn™ from Rohm & Haas); and modified methacrylate copolymers (e.g. HydroSal™ from Salvona Technologies); or mixtures thereof.

Suitable levels of malodor binding polymer are from about 0.01% to about 2%, alternatively from about 0.01% to about 1%, alternatively about 0.01% to about 0.8%, alternatively about 0.01% to about 0.6%, alternatively about 0.01% to about 0.1%, alternatively about 0.01% to about 0.07%, alternatively about 0.07%, by weight of the freshening composition. Compositions with higher amount of malodor binding polymer may make fabrics susceptible to soiling and/or leave unacceptable visible stains on fabrics as the solution evaporates off of the fabric.

Malodor Counteractant

The freshening composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces. For example, aliphatic aldehydes react with amine odors, such as fish and cigarette odors. When used in combination with the malodor binding polymer, the freshening composition may neutralize a broader range of malodor causing materials which, in turn, further reduces malodors in the air or on inanimate surfaces.

Specifically, the freshening composition includes a malodor counteractant: cyclodextrin and it can further comprise a malodor counteractant selected from the group consisting of: polyols, amine functional polymers, aldehydes, and combinations thereof. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof.

Buffering System

The freshening composition may include a buffering agent. The buffering agent may be an acidic buffering agent. The buffering agent may be a dibasic acid, carboxylic acid, dicarboxylic acid such as maleic acid, tricarboxylic acid such as citric acid, or a polycarboxylic acid such as polyacrylic acid. The carboxylic acid may be, for example, citric acid, polyacrylic acid, or maleic acid. The acid may be sterically stable. The acid may be used in the composition for maintaining the desired pH. The freshening composition may have a pH from about 4 to about 9, alternatively from about 4 to about 8.5, alternatively from about 4 to about 6.9, alternatively about 4 to about 6.7. Preferably, the buffer system comprises one or more buffering agents selected from the group consisting of: citric acid, maleic acid, polyacrylic acid, and combinations thereof. It has been found that buffer systems that include a buffering agent selected from the group consisting of: citric acid, maleic acid, polyacrylic acid, and combinations thereof provide stable freshening compositions with prolonged shelf life.

Preferably, the buffer system comprises citric acid and sodium citrate. It has been found that buffer systems comprising citric acid and sodium citrate provide stable freshening compositions with a prolonged shelf life.

The freshening compositions may include a secondary or tertiary amine. The freshening compositions may contain at least about 0%, alternatively at least about 0.001%, alternatively at least about 0.01%, by weight of the composition, of a buffering agent. The composition may also contain no more than about 2%, alternatively no more than about 0.75%, alternatively no more than about 0.5%, by weight of the composition, of a buffering agent.

Wetting Agent

The freshening composition may include a wetting agent that provides a low surface tension that permits the composition to spread readily and more uniformly on hydrophobic surfaces like polyester and nylon. It has been found that the freshening composition, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives and perfumes in the concentrated freshening compositions. Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as C12-18 aliphatic alcohols, are not generally compatible with the cyclodextrin. Certain of the block polymer surfactant compounds designated Pluronic™ and Tetronic™ by the BASF-Wyandotte Corp., Wyandotte, Michigan, are readily available.

Another suitable wetting agents that can be used in the present composition are the SILWET silicone polyethers. Nonlimiting examples of these silicone polyethers include the SILWET™ surfactants available from Momentive Performance Chemical, Albany, New York. Exemplary SILWET™ surfactants are as follows in Table 6 below. However, it will be appreciated that mixtures of the following surfactants may also be used in the present invention.

TABLE 6

| SIL WET ™ Surfactants | Average MW |
|---|---|
| L-7608 | 600 |
| L-7607 | 1,000 |
| L-77 | 600 |
| L-7605 | 6,000 |
| L-7604 | 4,000 |
| L-7600 | 4,000 |
| L-7657 | 5,000 |

The total amount of surfactants (e.g. solubilizer, wetting agent) in the freshening composition is from 0 to about 3%, alternatively from 0 to about 1%, alternatively from 0 to about 0.9%, alternatively from to about 0.7%, alternatively from 0 to about 0.5%, alternatively from 0 to 0.3% by weight of the composition. Compositions with higher concentrations can make fabrics susceptible to soiling and/or leave unacceptable visible stains on fabrics as the solution evaporates.

Setting Polymers

The composition of the present invention may further comprise one or more setting polymers, "setting polymer" means any polymer which refers to polymer having properties of film-formation, adhesion; or coating deposited on a surface on which the polymer is applied The setting polymer may be present at a level from about 00.5% to about 5%, by weight of the garment refreshing composition. The molecular weight of the setting polymer is preferably from 1,000 to 500,000, more preferably from 2,000 to 250,000 even more preferably from 5,000 to 200,000.

The setting polymer according to the present invention may be any water-soluble or water dispersible polymer. Preferably the polymer is a film-forming polymer or mixture of such polymers. This includes homopolymers or copolymers of natural or synthetic origin having functionality rendering the polymers water-soluble such as hydroxyl, amine, amide or carboxyl groups. The setting polymers may be cationic, anionic, non-ionic or amphoteric. The polymers make be a single species of polymer or a mixture thereof. Preferably the setting polymer is selected from: anionic polymers, non-ionic polymers, amphoteric polymers and mixtures thereof.

Anti-Wrinkle Agent

The compositions of the present invention may optionally comprise an anti-wrinkle agent which may comprise silicone and preferably this is in an emulsion. Silicone may be present at a level from about 0.5% to about 6%, by weight of the composition.

Structurant System

The freshening composition may include a structurant system having at least one structuring agent. The structuring agent may include one or more biopolymers. Non-limiting examples of such biopolymers include polysaccharides such as polymers of glucose, fructose, galactose, mannose, rhamnose, glucuronic acid and mixtures thereof.

The structurant system may be in the form of a polysaccharide system. Preferable polysaccharides include xanthan gum, glucomannan, galactomannan, and combinations thereof. The glucomannan may be derived from a natural gum such as konjac gum. The galactomannan may be derived from naturals gums such as locust bean gum. Polysaccharides may also include carrageenan. The gums may be modified such as by deacetylation.

The freshening composition may include a polysaccharide system comprising at least two polysaccharides, such as a first polysaccharide and a second polysaccharide. The first polysaccharide may be xanthan gum. The second polysaccharide may be selected from the group consisting of glucomannan, galactomannan, and combinations thereof. The second polysaccharide may be selected from the group consisting of tara gum, konjac gum, locust bean gum, and combinations thereof.

Preferably, the first polysaccharide is xanthan gum and the second polysaccharide is konjac gum.

The first polysaccharide may be present at a level of greater than 10% and less than 90%, alternatively about 20% to about 80%, alternatively about 40% to about 60%, by weight of the polysaccharide system.

The second polysaccharide may be present at a level of about 15% to about 85%, alternatively about 20% to about 80%, alternatively about 40% to about 60% by weight of the polysaccharide system.

The total concentration of polysaccharide present in the freshening composition may be less than about 0.5%, or preferably less than about 0.2%, or preferably less than about 0.1%, more preferably less than 0.08%, and most preferably less than 0.06%. Without wishing to be bound by theory, it is believed that minimizing the total polysaccharide level present in the freshening composition diminishes residue and/or optimizes spray characteristics.

The polysaccharide system may have a weight-average molecular weight in the range of about 10,000 Daltons to about 15,000,000 Daltons, alternatively about 200,000 Daltons to about 10,000,000 Daltons, alternatively about 300,000 Daltons to about 6,000,000 Daltons, alternatively about 300,000 Daltons to about 500,000 Daltons.

The polysaccharide system may be characterized by the average ratio of acetylation. The average ratio of acetylation may be in the range of about 2.0 to about 0.5, preferably in the range of about 1.5 to about 0.5.

The freshening composition may have a total protein level of less than about 100 parts per million (ppm), or less than 50 ppm, or less than 25 ppm, or less than 10 ppm. It may be desirable to limit the total protein level in the freshening composition in order to minimize discoloring of surfaces to which the freshening composition is applied.

Freshening Product

The freshening product comprises a spray dispenser. The spray dispenser may be transparent or translucent such that the freshening composition is visible or at least partially visible from outside of the freshening product.

The spray dispenser may hold various amounts of freshening composition. The spray dispenser may be capable of withstanding internal pressure in the range of about 20 p.s.i.g. to about 140 psig, alternatively about 80 to about 130 p.s.i.g. The total composition output and the spray droplet/particle size distribution may be selected to support the particulate removal efficacy but avoid a surface wetness problem. Total output is determined by the flow rate of the composition as it is released from the spray dispenser. To achieve a spray profile that produces minimal surface wetness, it is desirable to have a low flow rate and small 5 spray droplets.

The flow rate of the composition being released from the spray dispenser may be from about 0.0001 grams/second (g/s) to about 2.5 grams/second. Alternatively, the flow rate may be from about 0.001 grams/second to about 2.5 grams/second, or about 0.01 grams/second to about 2.0 grams/second. For an aerosol sprayer, the flow rate is determined by measuring the rate of composition expelled by a spray dispenser for any 60 second period of use.

The Sauter Mean Diameter of the spray droplets may be in the range of from about 10 μm to about 100 μm, alternatively from about 20 μm to about 60 μm. At least some of the spray droplets are sufficiently small in size to be suspended in the air for at least about 10 minutes, and in some cases, for at least about 15 minutes, or at least about 30 minutes. Small particles can be efficiently created when the spray is dispensed in a wide cone angle. For a given nozzle component and delivery tube, cone angles can be modified by varying the insertion depth of the nozzle in the delivery tube. The cone angle may be greater than about 20 degrees, or greater than about 30 degrees, or greater than about 35 degrees, or greater than about 40 degrees, or greater than about 50 degrees.

The spray dispenser may be configured to spray the freshening composition at an angle that is between an angle that is parallel to the base of the container and an angle that is perpendicular thereto. The desired size of spray droplets can be delivered by other types of spray dispensers that are capable of being set to provide a narrow range of droplet size. Such other spray dispensers include, but are not limited to: foggers, ultrasonic nebulizers, electrostatic sprayers, and spinning disk sprayers. The spray dispenser may be comprised of various materials, including plastic, metal, glass, or combinations thereof. The spray dispenser may be pressurized, unpressurized or non-aerosol.

A non-aerosol spray dispenser may include a pre-compression trigger sprayer.

One suitable non-aerosol spray dispenser is a plastic non-aerosol dispenser. The dispenser may be constructed of polyethylene such as a high-density polyethylene; polypropylene;

polyethyleneterephthalate ("PET"); vinyl acetate, rubber elastomer, and combinations thereof. The spray dispenser may be made of clear PET. Another suitable spray dispenser includes a continuous action sprayer, such as FLAIROSOL™ dispenser from Afa Dispensing Group. The FLAIROSOL™ dispenser includes a bag-in-bag or bag-in-can container with a pre-compression spray engine, and aerosol-like pressurization of the freshening composition. An example of the FLAIROSOL™ dispenser is described in U.S. Pat. No. 8,905,271B2.

A pressurized spray dispenser may include a propellant. Various propellants may be used. The propellant may comprise hydrocarbon(s); compressed gas(es), such as nitrogen, carbon dioxide, air; liquefied gas(es) or hydrofluoro olefin ("HFO"); and mixtures thereof. Preferably, the product comprises a propellant selected from the group consisting of compressed gas such as compressed air, compressed nitrogen, and combinations thereof. Propellants listed in the U.S. Federal Register 30 49 C.F.R. § 1.73.115, Class 2, Division 2.2 are considered acceptable. The propellant may particularly comprise a trans-1,3,3,3-tetrafluoroprop-1-ene, and optionally a CAS number 1645-83-6 gas. Such propellants provide the benefit that they are not flammable, although the freshening compositions are not limited to inflammable propellants. One such propellant is commercially available from Honeywell International of Morristown, New Jersey under the trade name HFO-5 1234ze or GWP-6. If desired, the propellant may be condensable. By "condensable", it is meant that the propellant transforms from a gaseous state of matter to a liquid state of matter in the spray dispenser and under the pressures encountered in use. Generally, the highest pressure occurs after the spray dispenser is charged with a freshening composition but before that first dispensing of that freshening composition by the user. A condensable propellant provides the benefit of a flatter depressurization curve as the freshening composition is depleted during usage.

The pressurized spray dispenser may be free of a hydrocarbon propellant. The freshening composition may be delivered from the spray dispenser which includes delivery components including but not limited to a valve to control flow and to seal the freshening composition within the spray dispenser, a button actuator and a nozzle for dispensing the freshening composition to the environment. The freshening composition may be contained in a bag-in-can plastic spray dispenser.

Spray Dispenser

The freshening compositions of the present invention can be contained in plastic containers constructed of hydrophilic perfume compatible materials. These materials avoid complexing, with hydroplilic perfume ingredients, such that absorption by and/or transmission through plastic containers is minimized. Suitable hydrophilic perfume compatible materials can be readily identified by determining the average hydrophilic perfume loss through gas chromatography analysis. Hydrophilic perfume compatible materials result in an average hydrophilic perfume ingredient loss of less than about 50% alternatively less than about 20%, alternatively less than about 15% and alternatively less than about 10% of the originally present individual hydrophilic perfume ingredients.

Freshening compositions containing a substantial amount of hydrophilic perfume ingredients can be stored in plastic container constructed of at least 80% hydrophilic perfume compatible materials for 8 weeks at ambient temperature. After storage, gas chromatography analysis is used to determine the amount of the various perfume ingredients remaining in the aqueous composition and approximate loss is calculated based on the amount of each ingredient originally present.

An effective amount of hydrophilic perfume compatible materials suitable for the present invention is at least about 80%, alternatively about 80% to about 100%, alternatively about 90% to about 100%, and alternatively 100%, by weight of the container. Non-limiting examples of hydrophilic perfume compatible materials are any resins of high density polyethylene (HDPE), low density polyethylene (LDPE), polyvinyl chloride (PVC), polypropylene (PP), polystyrene (PS), polyethylene-co-vinyl alcohol (EVOH), fluorinated polymer such as Aclar®, acrylonitrile-methyl acrylate copolymer such as Barex®, or mixtures thereof. Alternatively HDPE is utilized in the present invention.

In one embodiment, an HDPE bottle, from Plastipak Packaging Inc. Champaign, Ill., is used to contain the aqueous composition of the present invention. HDPE bottles can be made by any blow molding, injection molding, and thermoform process known in the art. For example, for blow molded bottles, heat softened HDPE is extruded as a hollow tube into a mold cavity and forced by pressurized air against the walls of the cold mold cavity to form the bottle. The bottle solidifies by cooling.

It has been found that the perfume compositions having a Clog P of less than about 3 are not fully absorbed into and/or transmitted through the hydrophilic perfume compatible materials such as PP and HDPE. Thus, this assists in preventing transmission of perfume ingredients through plastic containers; which in turn provides consumer noticeable longer lasting fragrance life.

Any of the hydrophilic perfume compatible materials can be used in conjunction with one or more barrier materials including amorphous carbon, silicone oxide or mixtures thereof and metallized coating.

Method of Use

The freshening composition can be used by dispersing, e.g., by placing the freshening composition into a dispenser, such as a spray dispenser and spraying an effective amount into the desired fabric. "Effective amount", when used in connection with the amount of the freshening composition, means an amount that provides neutralization of a malodor to the point that it is not discernible by the human sense of smell, yet not so much as to saturate or create a pool of liquid on an article or surface and so that, when dry, there is no visual deposit readily discernible. Dispersing can be achieved by using a spray device, a roller, a pad, or other product forms described hereinafter.

EXAMPLES

The following examples are intended to more fully illustrate the present invention and are not to be construed as limitations of the present invention since many variations thereof are possible without departing from the scope of the present invention. All parts, percentages and ratios used herein are expressed as percent weight unless otherwise specified.

Examples 1-2: Compositions

| Ingredient | Example 1 (wt %) | Example 2 (wt %) |
|---|---|---|
| Glycol phenyl ether (1) | 0.000 | 1.000 |
| Ethanol | 3.000 | 2.000 |
| Polyethyleneimine (2) | 0.065 | 0.065 |
| Silicone-based wetting agent (3) | 0.100 | 0.100 |
| Didecyldimethyl ammonium chloride (4) | 0.060 | 0.060 |
| Maleic Acid | 0.060 | 0.060 |
| Citric acid | 0.015 | 0.015 |
| Preservative (5) | 0.015 | 0.015 |
| Cyclodextrin (6) | 2.600 | 1.360 |
| Bacillus spores (7) | 0.100 | 0.200 |
| Water and minors | To 100% | To 100% |

(1) Dowanol EPh6—Dow
(2) Lupasol HF—BASF
(3) Silwet L-7600—Momentive
(4) Uniquat 2250—Lonza
(5) Koralone B-119—Dupont
(6) One or more beta cyclodextrins selected from hydroxypropyl beta-cyclodextrin (e.g. Cavasol ® W7 HP—Wacker), randomly methylated beta-cyclodextrin, hydroxyethyl alpha-cyclodextrin and hydroxyethyl beta-cyclodextrin, randomly methylated beta-cyclodextrin.
(7) Evozyme ® P500 BS7, Genesis Biosciences, Cardiff

Example 3

The following example evaluates the impact of cyclodextrin on growth of *Bacillus* spores on textile surfaces. This was accomplished by counting the colonies over time for two different treatments. The test was repeated 4 times to give a total of 4 replicates.

Treatment 1: 50% tryptic soy broth (product code: 22092, Sigma Aldrich) solution in DI (deionized) water.

Treatment 2: 50% tryptic soy broth (product code: 22092, Sigma Aldrich) solution, 1% beta-cyclodextrin (product code: 0006646, Carbosynth Ltd) in DI water.

Knitted cotton swatches were cut to 2 cm circles (Desized EQWKC1, Warwick Equest Ltd) and autoclaved to sterilize prior to testing. Swatches were placed in sterile petri-dishes and 400 μL of treatment solution was pipetted onto each one. Each swatch was then inoculated with 20 μL of a $5.24\times10^6$ cfu/mL *Bacillus* spores blend suspension. The *Bacillus* spores used were Evozyme® P500 BS7, Genesis Biosciences, Cardiff. Two of each fabric circles were placed with a sterile tweezer into 50 mL sterile centrifuge tubes and lids were screwed. The tubes were then stored in a 35°) C. oven. Samples were taken at 2, 4 and 6 hours. The fabrics were vortexed with 9 mL of physiological water (product reference: AEB110389, 0.85%, Biomerieux) for 30 s. Sample solutions were serially diluted 1:10 into physiological water, plated onto Tryptone Soya Agar (product reference: 8084, Southern Group Laboratory Limited) and incubated at 35° C. for 24 hours before counting colonies.

The table below contains the spore count over time. Treatment 2, in accordance with the invention, shows significantly more colonies than treatment 1 after 4 hours and 8 hours which shows that cyclodextrin improves *Bacillus* growth.

| | Colony count over time (cfu/mL) | | | | | |
|---|---|---|---|---|---|---|
| | 2 h incubation | | 4 h incubation | | 6 h incubation | |
| | Average | Standard error | Average | Standard error | Average | Standard error |
| Treatment 1 (Comparative) | 7.13E+3 | 6.25E+2 | 3.58E+4 | 1.01E+3 | 4.46E+5 | 8.96E+4 |
| Treatment 2 (Invention) | 6.0E+3 | 3.54E+2 | 8.58E+4 | 7.33E+3 | 3.98E+6 | 3.26E+5 |

Example 4

Cyclodextrin can absorb volatile compounds causing malodor. A malodor test was completed to determine whether *Bacillus* spores have an impact on the cyclodextrin anti-malodor benefit.

Knitted cotton swatches were cut to 5 cm square (Desized EQWKC1, Warwick Equest Ltd). Fabric and glass jars were autoclaved to sterilize prior to testing.

Malodor sources were absorbed by the knitted cotton swatch in a 50 mL glass jar (10 swatches per jar). The swatches were left with the malodor source in the sealed jar for 4 days at room temperature, the fabric wasn't in contact with the malodor source. Each swatch was then transferred to a 60 mL glass jar for 3 days at room temperature.

| | |
|---|---|
| Malodor source 1 | 10 cigarette butts (Golden Virginia hand rolling tobacco) |
| Malodor source 2 | 10 g garlic granule mixed with 5 g water (UPC code: 832405, Schwartz) |

Treatments were sprayed in the 60 mL jar containing the swatch, 1 stroke per jar (Burk spray bottle TurnNSpray 250 mL, amount sprayed per stroke: 1.2 mL, Lab Unlimited, catalogue number: 6.252 153).

| Treatment 0 | DI water |
|---|---|
| Treatment 1 | 1% Beta-cyclodextrin (product code: OC06646, Carbosynth Ltd) in DI water |
| Treatment 2 | 1% Beta-cyclodextrin (product code: OC06646, Carbosynth Ltd) in $8.12\times10^6$ cfu/mL Bacillus Spores blend (Evozyme ® P500 BS7, Genesis Biosciences, Cardiff) |

Samples with Treatment 1 and Treatment 2 were labelled with random number for 3 panelists. Each panelist had 1 replicate of each treatment for both malodor source. Treatment 1 and Treatment 2 were compared to Treatment 0 and grade by the panelists (0=No preference, 4=it's very much better than Treatment 0).

The table below with the panelist grades shows that Treatment 2 average is higher for both malodor sources. We can therefore conclude that the *Bacillus* spores do not negatively impact the malodor performance of the cyclodextrin.

| | | Panelist 1 | Panelist 2 | Panelist 3 | Average |
|---|---|---|---|---|---|
| Malodor source 1 | Treatment 1 (Comparative) | 2 | 1 | 1 | 1.33 |
| | Treatment 2 (Invention) | 2 | 2 | 2 | 2.00 |
| Malodor source 2 | Treatment 1 (Comparative) | 1 | 1 | 2 | 1.33 |
| | Treatment 2 (Invention) | 3 | 2 | 2 | 2.33 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fabric freshening composition comprising:

a) from about $1\times10^2$ to about $1\times10^9$ CFU/g of the composition, of bacterial spores, wherein the bacterial spores comprise *Bacillus* spores;

b) a cyclodextrin; and c) a polysaccharide system comprising a first polysaccharide and a second polysaccharide, wherein the polysaccharide system has a weight-average molecular weight in the range of about 200,000 Daltons to about 10,000,000 Daltons.

2. The composition according to claim 1, wherein the bacterial spores comprise *Bacillus subtilis, Bacillus amyloliquefaciens, Bacillus licheniformis, Bacillus megaterium, Bacillus pumilus, Bacillus cereus, Bacillus thuringiensis, Bacillus mycoides, Bacillus tequilensis, Bacillus vallismortis, Bacillus mojavensis* and mixtures thereof.

3. The composition according to claim 1 wherein the *Bacillus* is selected from the group consisting of *Bacillus subtilis, Bacillus amyloliquefaciens, Bacillus licheniformis, Bacillus megaterium, Bacillus pumilus*, and mixtures thereof.

4. The composition according to claim 1, wherein the composition is an aqueous composition comprising from 90% to 99.5% by weight of the composition of water.

5. The composition according to claim 1, wherein the composition further comprises from about 0.002% to about 3% by weight of the composition of perfume.

6. The composition according to claim 1, wherein the composition comprises from about 0.002% to about 3% by weight of the composition of perfume, wherein the perfume comprises about 60% or more, by weight of the perfume, of perfume raw materials having a ClogP greater than 1.0.

7. The composition according to claim 1, wherein the bacterial spores are in particulate form and wherein the first polysaccharide is xanthan gum, and wherein the second polysaccharide is selected from the group consisting of tara gum, konjac gum, locust bean gum, and combinations thereof.

8. The composition according to claim 1, wherein the bacterial spores are in particulate form and wherein the first polysaccharide is present at a level of greater than 10% and less than 90%, by weight of the polysaccharide system.

9. The composition according to claim 8, wherein the first polysaccharide is present at a level of about 40% to about 60%, by weight of the polysaccharide system.

10. The composition according to claim 1, wherein the polysaccharide system has a weight-average molecular weight in the range of about 300,000 Daltons to about 500,000 Daltons.

11. The composition according to claim 1, wherein the bacterial spores are in particulate form and wherein the total polysaccharide level of the composition is less than 0.5% by weight of the composition.

12. The composition according to claim 1, wherein the composition further comprises from 0.01% to 3% by weight of the composition of a surfactant selected from the group consisting of nonionic surfactants, cationic surfactants, amphoteric surfactants, zwitterionic surfactants, and mixtures thereof.

13. The composition according to claim 1, wherein the composition further comprises from about 0.01% to about 5% of a solvent by weight of the composition, wherein the solvent is selected from the group consisting of an alcohol, a polyol, and mixtures thereof.

14. The composition according to claim 1, wherein the composition further comprises a wetting agent and an anti-wrinkle agent.

15. The composition according to claim 1, wherein the composition further comprises a malodor counteractant selected from the group consisting of polyols, amine functional polymers, aldehydes, and combinations thereof.

16. A product comprising a composition according to claim 1 and a spray device wherein the spray device is made of plastic.

17. The product of claim 16, wherein the plastic is selected from the group consisting of: polypropylene, polyethylene terephthalate, high density polyethylene, and combinations thereof.

18. A method of freshening a fabric comprising the step of treating the fabric with a composition according to claim 1.

19. The composition according to claim 1, wherein the cyclodextrin is present at a concentration of about 1% by weight.

* * * * *